United States Patent
Pruksachatkun et al.

(10) Patent No.: US 11,861,314 B2
(45) Date of Patent: Jan. 2, 2024

(54) EXTRACTING CLINICAL FOLLOW-UPS FROM DISCHARGE SUMMARIES

(71) Applicant: ASAPP, INC., New York, NY (US)

(72) Inventors: Yada Pruksachatkun, New York, NY (US); Sean Adler, New York, NY (US); Thomas Gregory McKelvey, Jr., New York, NY (US); Jordan Louis Swartz, New York, NY (US); Hui Dai, New York, NY (US); Yi Yang, Long Island City, NY (US); David Sontag, Brookline, MA (US); Jennifer Marie Seale, Austin, TX (US)

(73) Assignee: ASAPP, INC., New York, NY (US)

( * ) Notice: Subject to any disclaimer, the term of this patent is extended or adjusted under 35 U.S.C. 154(b) by 475 days.

(21) Appl. No.: 17/221,485

(22) Filed: Apr. 2, 2021

(65) Prior Publication Data

US 2021/0312128 A1   Oct. 7, 2021

Related U.S. Application Data

(60) Provisional application No. 63/004,901, filed on Apr. 3, 2020.

(51) Int. Cl.
| | |
|---|---|
| *G06F 40/30* | (2020.01) |
| *G06F 40/284* | (2020.01) |
| *G16H 10/60* | (2018.01) |
| *G16H 10/40* | (2018.01) |
| *G06N 3/04* | (2023.01) |
| *G06F 18/2431* | (2023.01) |
| *G06V 20/62* | (2022.01) |

(52) U.S. Cl.
CPC .......... *G06F 40/30* (2020.01); *G06F 18/2431* (2023.01); *G06F 40/284* (2020.01); *G06N 3/04* (2013.01); *G16H 10/40* (2018.01); *G16H 10/60* (2018.01); *G06V 20/62* (2022.01)

(58) Field of Classification Search
USPC ............................................... 704/7–10, 257
See application file for complete search history.

(56) References Cited

U.S. PATENT DOCUMENTS

| | | | |
|---|---|---|---|
| 2017/0193197 A1* | 7/2017 | Randhawa | ............. G16H 10/60 |
| 2019/0102380 A1* | 4/2019 | Huang | .................... G06F 40/30 |
| 2021/0183484 A1* | 6/2021 | Shaib | .................... G06F 40/295 |

OTHER PUBLICATIONS

Alsentzer, Emily, et al., "Extractive summarization of EHR discharge notes", CoRR, abs/1810.12085, URL http://arxiv.org/abs/1810.12085, 2018, 8 pages.

(Continued)

*Primary Examiner* — Leonard Saint-Cyr
(74) *Attorney, Agent, or Firm* — GTC Law Group PC & Affiliates

(57) ABSTRACT

Medical records may be analyzed to identify important items in the text of the medical record. Actionable content may be identified and may be emphasized or extracted from the medical record. Actionable content may be categorized into one or more categories. Identification may include processing using trained models that use contextual information and position information to determine sentence labels.

18 Claims, 12 Drawing Sheets

(56) References Cited

OTHER PUBLICATIONS

Alsentzer, Emily, et al., "Publicly available clinical BERT embeddings", In Proceedings of the 2nd Clinical Natural anguage Processing Workshop, Minneapolis, Minnesota, USA, Association for Computational Linguistics, URL https://www.aclweb.org/anthology/W19-1909, 2019, pp. 72-78.

Baron, Richard J, "What's keeping us so busy in primary care? A snapshot from one practice.", The New England Journal of Medicine, 2010, pp. 1632-1636.

Chen, Qingyu, et al., "Biosentvec: creating sentence embeddings for biomedical texts", 2019, 5 pages.

Devlin, Jacob, et al., "BERT: pre-training of deep bidirectional transformers for language understanding", CoRR, abs/1810.04805, URL http://arxiv.org/abs/1810.04805, arXiv:1810.04805v2 [cs.CL], May 24, 2019, 16 pages.

Doddington, George R, et al., "The Automatic Content Extraction (ACE) Program—Tasks, Data, and Evaluation", LREC, 2004, pp. 837-840.

Farri, Oladimeji, et al., "Effects of time constraints on clinician-computer interaction: A study on information synthesis from ehr clinical notes", Journal of Biomedical Informatics, 2013, pp. 1136-1144.

Gong, Jen J, et al., "Learning to summarize electronic health records using cross-modality correspondences", Proceedings of the 3rd Machine Learning for Healthcare Conference, vol. 85 of Proceedings of Machine Learning Research, URL http://proceedings.mlr.press/v85/gong18a.html Palo Alto, California Aug. 17-18, 2018. PMLR, Aug. 2018, pp. 551-570.

Jackson, Carlos T, et al., "Timeliness of outpatient follow-up: an evidence-based approach for planning after hospital discharge", Annals of family medicine, vol. 13, No. 2, 2015, pp. 115-122.

Jagannatha, Abhyuday, et al., "Overview of the first natural language processing challenge for extracting medication, indication, and adverse drug events from electronic health record notes (made 1.0)", Drug Safety, 2019, pp. 99-111.

Johnson, Alistair E.W, et al., "Mimic-iii, a freely accessible critical care database", Scientific Data, 3:160035, 2016, 9 pages.

Kripalani, Sunil, et al., "Deficits in communication and information transfer between hospital-based and primary care physicians: implications for patient safety and continuity of care", JAMA, vol. 297, No. 8, 2007, pp. 831-841.

Lafferty, John D, et al., "Conditional Random Fields: Probabilistic Models for Segmenting and Labeling Sequence Data", ICML, Jun. 2001, 10 pages.

Lample, Guillaume, et al., "Neural architectures for named entity recognition", HLT-NAACL, arXiv: 1603.01360v3 [cs.CL], Apr. 7, 2016, 11 pages.

Lee, Jinhyuk, "Biobert: a pre-trained biomedical language representation model for biomedical text mining", Bioinformatics, 2019, CoRR, abs/1901.08746, URL http://arxiv.org/abs/1901.08746, 2019, 7 pages.

Liang, Jennifer, et al., "A novel system for extractive clinical note summarization using EHR data", Proceedings of the 2nd Clinical Natural Language Processing Workshop, Minneapolis, Minnesota, USA—Association for Computational Linguistics doi: 10.18653/v1/W19-1906 RL https://www.aclweb.org/anthology/W19-1906, Jun. 2019, pp. 46-54.

Liu, Xiangan, et al., "Unsupervised pseudo-labeling for extractive summarization on electronic health records", CoRR, abs/1811.08040, URL http://arxiv.org/abs/1811.08040, Nov. 26, 2018, 8 pages.

Moore, Carlton, et al., "Tying up loose ends: discharging patients with unresolved medical issues", Archives of Internal medicine, vol. 167, 2007, pp. 1305-1311.

Mullenbach, James, et al., "CLIP: A Dataset for Extracting Action Items for Physicians from Hospital Discharge Notes", arXiv:2106.02524v1 [cs.CL], https://arxiv.org/pdf/2106.02524.pdf, Jun. 4, 2021, 14 pages.

Mulyar, Andriy, et al., "Phenotyping of clinical notes with improved document classification models using contextualized neural language models", ArXiv, abs/1910.13664, 2019, 6 pages.

Narayan, Shashi, et al., "Ranking sentences for extractive summarization with reinforcement learning", CoRR, abs/1802.08636, URL http://arxiv.org/abs/1802.08636, 2018, 13 pages.

Nestor, Bret, et al., "Feature robustness in non-stationary health records: Caveats to deployable model performance in common clinical machine learning tasks", Proceedings of Machine Learning Research vol. 106, ArXiv, abs/1908.00690, 2019, pp. 1-23.

Pradhan, Sameer, et al., "CoNLL-2012 shared task: Modeling multilingual unrestricted coreference in OntoNotes", Joint Conference on EMNLP and CoNLL—Shared Task Jeju Island, Korea—Association for Computational Linguistics. URL https://www.aclweb.org/anthology/W12-4501, Jun. 2012, pp. 1-40.

Segura-Bedmar, Isabel, "Semeval-2013 task 9: Extraction of drug-drug interactions from biomedical texts (ddiextraction 2013)", Second Joint Conference on Lexical and Computational Semantics (SEM), vol. 2: Seventh International Workshop on Semantic Evaluation (SemEval 2013), Atlanta, Georgia, Jun. 14-15, 2013, pp. 341-350.

Singh, Hardeep, et al., "Information overload and missed test results in electronic health record-based settings", JAMA internal medicine, vol. 173, No. 8, 2013, 4 pages.

Sinsky, Christine, et al., "Allocation of Physician Time in Ambulatory Practice: A Time and Motion Study in 4 Specialties", Annals of Internal Medicine, vol. 165, No. 11, https://adfm.org/media/1476/ann-2016-time-study.pdf, 2016, pp. 753-760.

Spencer, Rachel A, et al., "Processing discharge summaries in general practice: a qualitative interview study with gps and practice managers", BJGP, https://doi.org/10.3399/bjgpopen18X101625, 2019. URL https://bjgpopen.org/content/3/1/bjgpopen18X101625.abstract., 2019, 12 pages.

Sun, Weiyi, et al., "Evaluating temporal relations in clinical text: 2012 i2b2 challenge", Journal of the American Medical Informatics Association : JAMIA, vol. 20, No. 5, 2013, pp. 806-813.

Tai-Seale, Ming, et al., "Electronic Health Record Logs Indicate That Physicians Split Time Evenly Between Seeing Patients And Desktop Medicine", Health Aff (Millwood), vol. 36, No. 4, doi: 10.1377/hlthaff.2016.0811, Apr. 1, 2017, pp. 655-662.

Thiagarajan, Jayaraman J, et al., "Understanding behavior of clinical models under domain shifts", arXiv:1809.07806v2 [stat.ML], Jun. 14, 2019, 4 pages.

Uzuner, Ozlem, et al., "2010 i2b2/va challenge on concepts, assertions, and relations in clinical text", Journal of the American Medical Informatics Association : JAMIA, vol. 18, No. 5, 2011, pp. 552-556.

Uzuner, Ozlem, et al., "Evaluating the state of the art in coreference resolution for electronic medical records", Journal of the American Medical Informatics Association : JAMIA, vol. 19, No. 5, 2012, pp. 786-791.

Uzuner, Ozlem, et al., "Extracting medication information from clinical text", Journal of the American Medical Informatics Association : JAMIA, vol. 7, No. 5, 2010, pp. 514-518.

Were, Martin C, et al., "Natural language processing to extract follow-up provider information from hospital discharge summaries", https://www.ncbi.nlm.nih.gov/pmc/articles/PMC3041312/, 2010, 5 pages.

Zhang, Yijia, et al., "Biowordvec, improving biomedical word embeddings with subword information and mesh", Scientific Data 6:52, https://doi.org/10.1038/s41597-019-0055-0, 2019, 9 pages.

\* cited by examiner

EXTRACTING CLINICAL FOLLOW-UPS FROM DISCHARGE SUMMARIES

CLAIM OF PRIORITY

This patent application claims the benefit of U.S. Patent Application Ser. No. 63/004,901, filed Apr. 3, 2020, and entitled "DATASET FOR EXTRACTING CLINICAL FOLLOW-UPS FROM DISCHARGE SUMMARIES".

The content of the foregoing application is hereby incorporated by reference in its entirety for all purposes.

BACKGROUND

Transitioning patient care from hospitals to primary care providers (PCPs) can frequently result in medical errors. When patients are discharged, they often require pending actions to be followed up on by their PCP, who manages their long-term health, such as reviewing results for lab tests once they are available. Yet PCPs often have many patients and little time to review new clinical documents related to a recent hospital stay.

BRIEF DESCRIPTION OF THE FIGURES

The invention and the following detailed description of certain embodiments thereof may be understood by reference to the following figures.

DETAILED DESCRIPTION

Continuity of care is crucial to ensuring good outcomes for patients discharged from an inpatient hospital setting. Hospital discharge summaries are written records of the care provided to patients during hospitalization, and these records are an important source of pending tasks for primary care providers. Discharge summaries describing a hospital stay contain crucial information and action items to share with patients and their future caregivers. However, discharge summaries are often lengthy documents written as free-text with no universal structure. Caregivers often have many patients and little time to review new clinical documents and may fail to identify important pending tasks.

Systems and methods are described herein that identify important follow-up items from medical records. Medical records, such as discharge summaries, electronic health records (EHR), doctor notes, and the like may be processed to identify important items. Important items may include follow-up items such as medications, prescriptions, appointments, lab tests, and the like. Important items may be identified and emphasized in the medical record and/or extracted from the medical record. The identified important items may be presented to the physician or other relevant party.

Extracting follow-up items could have several direct benefits. First, it could improve patient safety by increasing primary care provider's overall recall of important follow-up tasks. Second, it might decrease the amount of time required to achieve that recall, which is critical as physicians are forced to spend an ever-increasing amount of time interacting with electronic health record (EHR) systems. And thirdly, a working system may integrate with EHRs to automatically address certain follow-ups, improving EHR usability and further reducing medical error.

In some examples, it has been observed that medical records such as discharge summary text mostly include information not directly actionable for follow-up. In some cases, extracting the actionable information for review by PCPs could reduce the amount of text they need to read by 88% or more.

Figure 1:
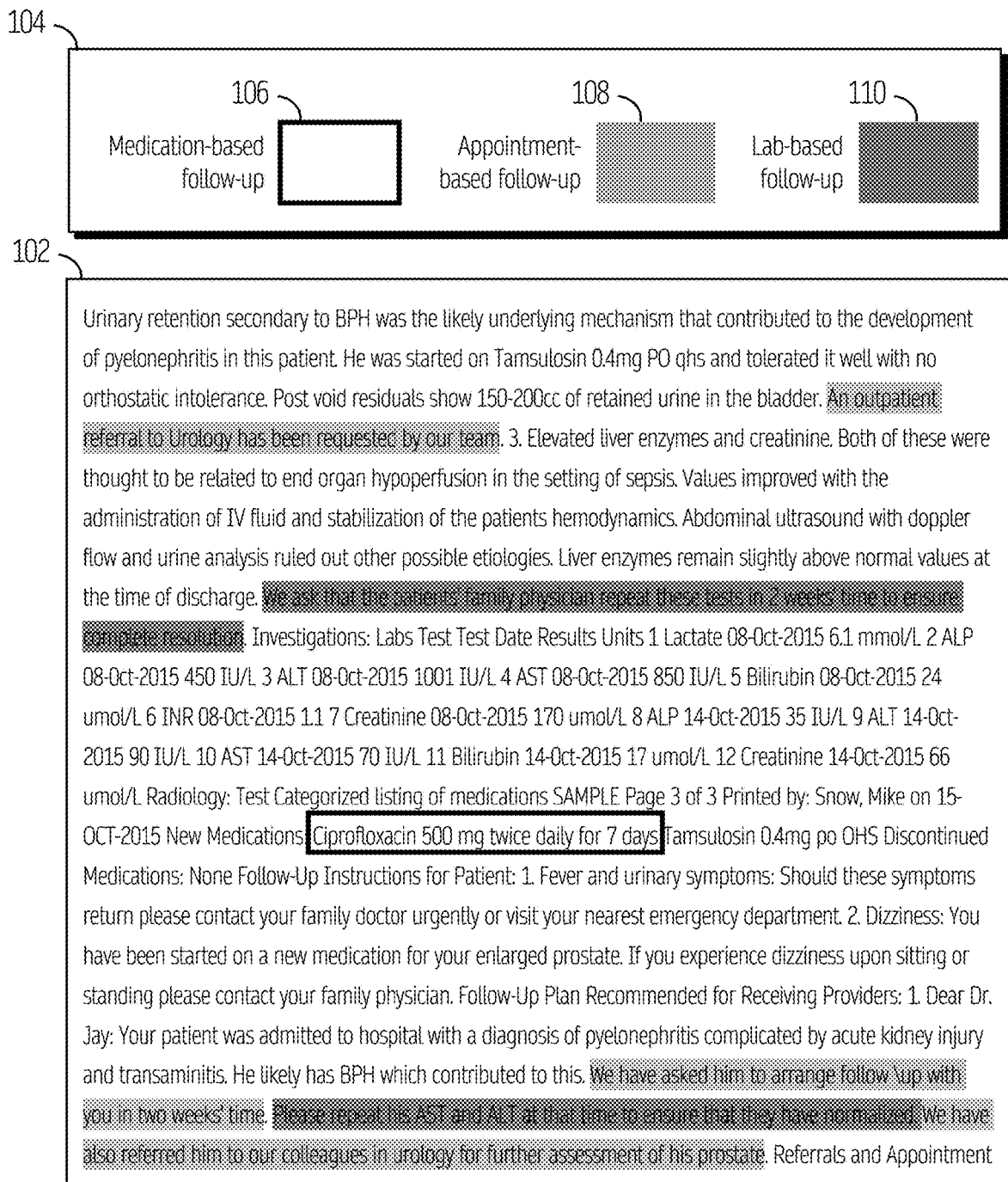
FIG. 1 depicts an illustrative detail of an example discharge summary with identification of important items.

FIG. 1 depicts aspects of one example of identification of important items from a discharge summary. In one example, a discharge summary 102 may include free text. In some cases, a discharge summary may include one or multiple pages of text. A physician reading the discharge summary may be required to quickly identify actionable or important items such as recommended appointments, medications, and required laboratory tests. Identifying the important items in the text may require significant time and concentration from the physician and important items may be easily missed. In embodiments, the methods and systems described herein may automatically identify important items in the discharge summary. The identified items may be emphasized within the text to allow the physician to quickly see and find the important items in the medical record. In one example, the identified important items may be highlighted within the discharge summary text. In one example, important items may be categorized into different categories 104 of important items and the different colors, textures, outlines, and the like may be used to identify and differentiate between the different categories of important items. FIG. 1 shows a discharge summary where the important items are categorized into three categories: medical-based follow-up 106, appointment-based follow-up 108, and lab-based follow-up 110. Important items within the discharge summary text 102 may be highlighted using colors that correspond to each of the categories 106, 108, 110. The highlights within the discharge summary text 102 may allow a physician to quickly identify the important and actionable item in the context of the medical record.

The success of the identification of important data in a medical record requires the identification and consideration of numerous subtleties associated with records. For example, for important data related to appointments, it may be desirable to leave out sentences that refer to "as needed" appointments, e.g., "See your endocrinologist as needed." As another example, for important data related to medications, it may be desirable to exclude sentences describing simple additions to the medication list, e.g., "Discharged on glargine 10u at bedtime," as these typically do not require further action. As another example, for important data related to medications, it may be desirable to include sentences that related to instructions to hold and restart medications, new medications with an end date (e.g., antibiotics), and medications requiring dosage adjustment (e.g. " . . . the plan is to keep patient off diuretics with monitoring of his labs and reinstitution once the kidney function improves").

In embodiments, the identified important items in a medical record (such as a discharge summary) may be extracted in addition or instead of being emphasized within the medical record. Important items may be extracted and shown/displayed to a physician outside of the medical record, wherein only the identified important items are shown. In some cases, the extracted important items may be shown categorized according to the categorization of the important items. In some embodiments, the identified items may be tagged within the medical record and/or extracted and used by other systems to automatically address certain important items such as scheduling appointments, lab tests, ordering medications, and the like.

In embodiments, identification of important items (such as actionable information) may include multi-label sentence classification. The labels generated by the multi-label classification may represent a type of action to be taken. In embodiments, important items such as follow-up items may fall into more than one category. For example, a sentence relating to scheduling imaging accompanied by a procedure or medication instructions may be related to multiple categories of important items. It is important to note that the methods and systems described herein differ from techniques related to mere document summarization. A summary of a document is generally constrained by size, coverage, scope, and the like and is not concerned with identifying all actionable content in the document. Known document summarization can miss and ignore actionable content and are not suitable for the identification of important items.

Figure 2:
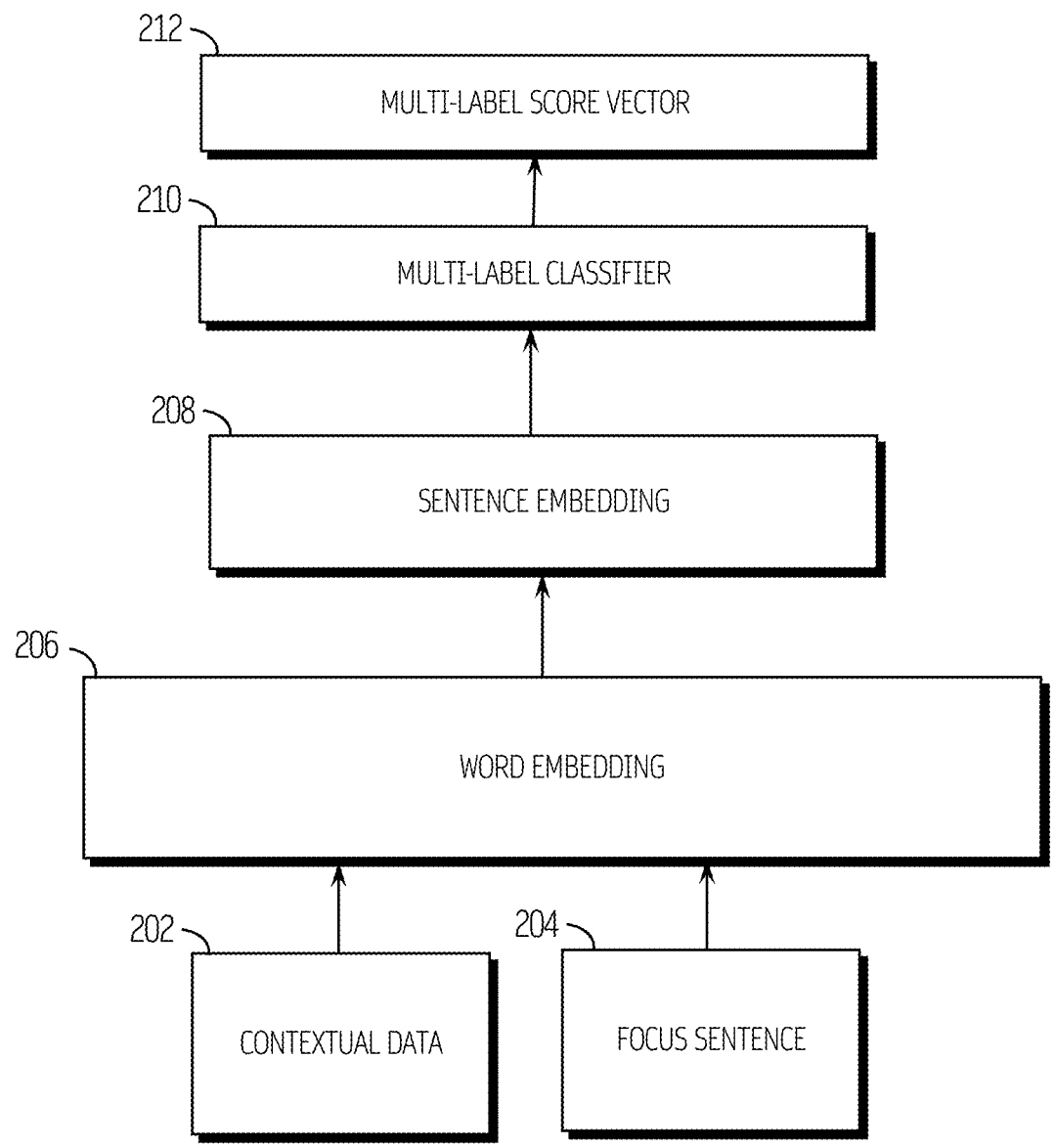
FIG. 2 is a schematic diagram depicting one example embodiment for multi-label sentence classification.

FIG. 2 shows aspects of one example embodiment of a system for multi-label sentence classification. The system may receive words or sentences from the medical record. In one example, the system may receive a sentence 204 from the medical record, and the system may output a multi-label score vector 210 that identifies if the sentence 204 (also referred herein as the focus sentence) is related to an important item and may also identify one or more categories of important items. In embodiments the sentence 204 may be a full sentence from the medical record, may be a partial sentence (such as a phrase), a group of consecutive words, or a plurality of sentences. In embodiments, the system may further receive contextual data 202 related to the focus sentence 204. In embodiments, the contextual data 202 may be sentences, sequential words, and the like that appear around the focus sentence 204 in the medical record. In one embodiment, the contextual data may be one or more sentences that appear directly before the focus sentence and/or one or more sentences that appear directly after the focus sentence in the medical record. In some cases, context data may include metadata associated with the text of the medical record. In some cases, structured data associated with the text of the medical records (lists of medications, patient data, dates, etc.) may be used as context data. The focus sentence 204 and the contextual data 202 may be provided to the system as parallel inputs.

The system may receive the contextual data 202 and the focus sentence 204 and process the contextual data 202 and the focus sentence 204 using a word embedding model 206.

The word embeddings model 206 may be a trained machine learning model. In some cases, the word embedding model may be a transformer-based machine learning model. The word embedding model 206 may be pretrained to take into account the context for each occurrence of a word in a focus sentence. In one embodiment, the word embedding model 206 may be based on pre-trained language models such as a Bidirectional Encoder Representations from Transformers (BERT) model, GPT-2, GPT-3, XLNet, RoBERTa, and the like. The word embedding model 206 may include a plurality of layers and/or hidden states.

The output of the word embedding model 206 may provide an embedding of the words of the focus sentence 204. In some embodiments, where the input to the word embedding model includes contextual data 202, the output of the word embedding model may provide contextual embedding of the words of the focus sentence. In one example, the word embedding model 2006 may generate one vector embedding output for each word or a pair of words in the focus sentence. In embodiments, the vector embeddings may be generated based on one or more intermediate outputs (vectors from intermediate layers and/or hidden layers) of the word embedding model 206.

An embedding is a representation of a token (such as a word, sentence, group of words) in a vector space such that the token embedding includes relevant information about the token. For example, in some implementations, a token embedding may embody information about the meaning of the token. Two tokens that have similar meanings may have token embeddings that are close to each other in the vector space. By contrast, two tokens that do not have similar meanings may have token embeddings that are not close to each other in the vector space. The embeddings may be contextual. Where embeddings are contextual, the embedding of a token may depend on previous or subsequent tokens (such as previous or subsequent sentences/words in the contextual data 202). For example, the token "cold" in the phrases "apply a cold compress" and "patient has a cold" may have different values according to the two very different meanings of "cold."

The system may include a sentence embedding model 208. The sentence embedding model 208 may receive the output of the word embedding model 206 and determine sentence embeddings. The sentence embedding model 208 may receive word embeddings (such as a contextual word embedding of the focus sentence 204). In embodiments, the sentence embedding model may be a trained machine mode such as a convolution neural network (CNN), a recurrent neural network, and the like. In one example, the sentence embedding model 208 may generate one-sentence embedding for the whole focus sentence 204. In one example, one sentence embedding may be determined by averaging the word embeddings generated by the word embedding model 206. In some embodiments, the sentence embedding model 208 may generate sentence embeddings based on special token embeddings generated by the word embedding model 206. For example, the word embedding model may be a BERT-type model that may receive special tokens as inputs and may generate embeddings of the special tokens at the output. The sentence embedding model 208 may process the embeddings of the special tokens generated by the word embedding mode 206 and generate sentence embeddings.

In one example, the system includes a multi-label classifier 210. The multi-label classifier may be a linear classifier that may be configured to determine a multi-label score vector 212 wherein each value of the score vector 212 identifies a score that provides a measure of whether the focus sentence 204 belongs to a category of important items that should be emphasized or extracted from a medical record. In embodiments, the multi-label classifier may be a logistic regression classifier and may include a linear layer followed by a sigmoid function. The multi-label score vector 212 may be a confidence score relating to how likely the focus sentence relates to an important item or actionable item. In embodiments, each value of the score vector 212 may correspond to a different category of important items. In some embodiments, a threshold value for each element of the vector may be used to determine if the focus sentence should be classified as an important item. For example, the score vector 212 may include four elements. Each element of the vector may be in the range of [0,1]. Each element of the vector may be associated with a threshold value and a category. The threshold value may indicate a value for each element above which the focus sentence may be classified as an important item for the respective category. In another embodiment, a function of two or more elements of the score vector may be used to determine if the focus sentence relates to an important item and/or what category of important items it relates to.

The system of FIG. 2 may be used to sequentially process a plurality of sentences in a medical record. The system may start with the first sentence as the focus sentence followed by selecting the second sentence as the focus sentence, and so on. In some cases, multiple instances of the system may be parallelized to allows the processing of multiple sentences from the medical record in parallel. In some cases, the system may be scaled such that the focus sentence may be the complete medical record comprising multiple sentences, and the system may label all the sentences in the medical record in parallel.

Figure 3:
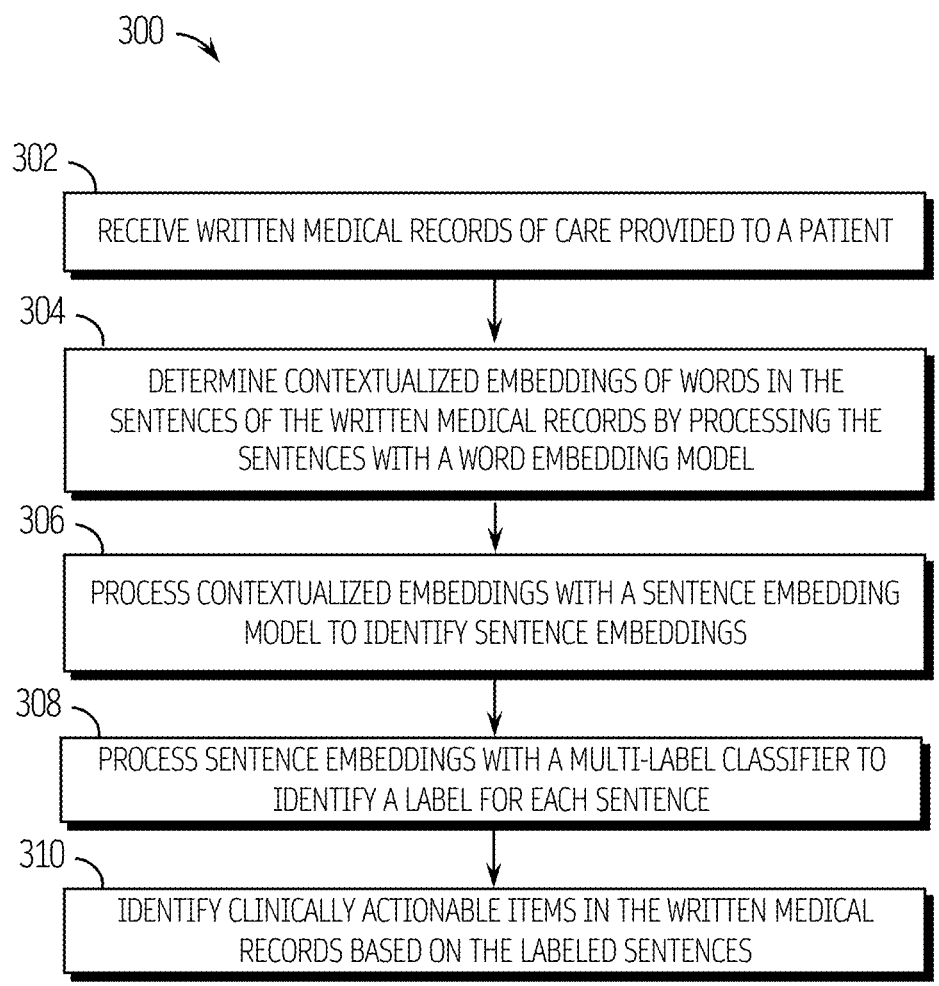
FIG. 3 is a flow diagram of a method for identifying important items from a medical record.

FIG. 3 depicts aspects of a method for identifying important items from a medical record. The method may include receiving written medical records of care provided to a patient 302. The medical records may be received from one or more health record systems. In some cases, the health records may be combined from different providers based on associated dates with the records. In some embodiments, the medical records may be preprocessed to filter extraneous data (such as irrelevant dates, codes, data providers) tokenize the elements (dividing text into sentences, words, phrases, sub-words, etc.). For example, tokenization may include dividing a word into sub-words to reduce the number of vocabulary items (for example, "talking" can be broken down into sub-words "talk" and "ing"). The method may further include determining contextualized embeddings of words in the sentences of the written medical records by processing the sentences with a trained machine model 304. The trained machine model may be a word embedding model. The model may identify embeddings of sentences and/or words by processing the sentences and contextually associated with the sentences and/or words. In some cases, the contextual data may include sentences and/or words that occurred before (to the left) or after (to the right) of the sentence. The embeddings may be further processed with a sentence embedding model 306. The sentence embedding model may identify sentence embeddings which may be processed by a multi-label classifier that may be configured to identify a label for each sentence in the medical record 308. In some embodiments, the label may be a score vector. The method may further include identifying clinically actionable items in the written medical records based on the labeled sentences 310. The identified actionable items may be emphasized within the medical record when viewed by a physician on an electronic device. The emphasis may include highlighting, changing the color of text, background, blinking, visual effects, and the like.

In some embodiments, users viewing medical records may be provided with selection options for highlighting identified important items, choosing to only see the identified important items, selecting categories of important items to show and/or highlight. In some cases, users may be provided with selection options for selecting and/or dismissing individual or one or more groups of sentences that were identified as important items or not identified as important. The selection and/or dismissal of selections may be used to refine models. The selection and/or dismissal of selections may be used as additional training data for training models used to identify the important items. Various interfaces such as pen-based selections, checkboxes, list boxes, and the like may be used to make selections and/or dismiss selections.

Figure 4:
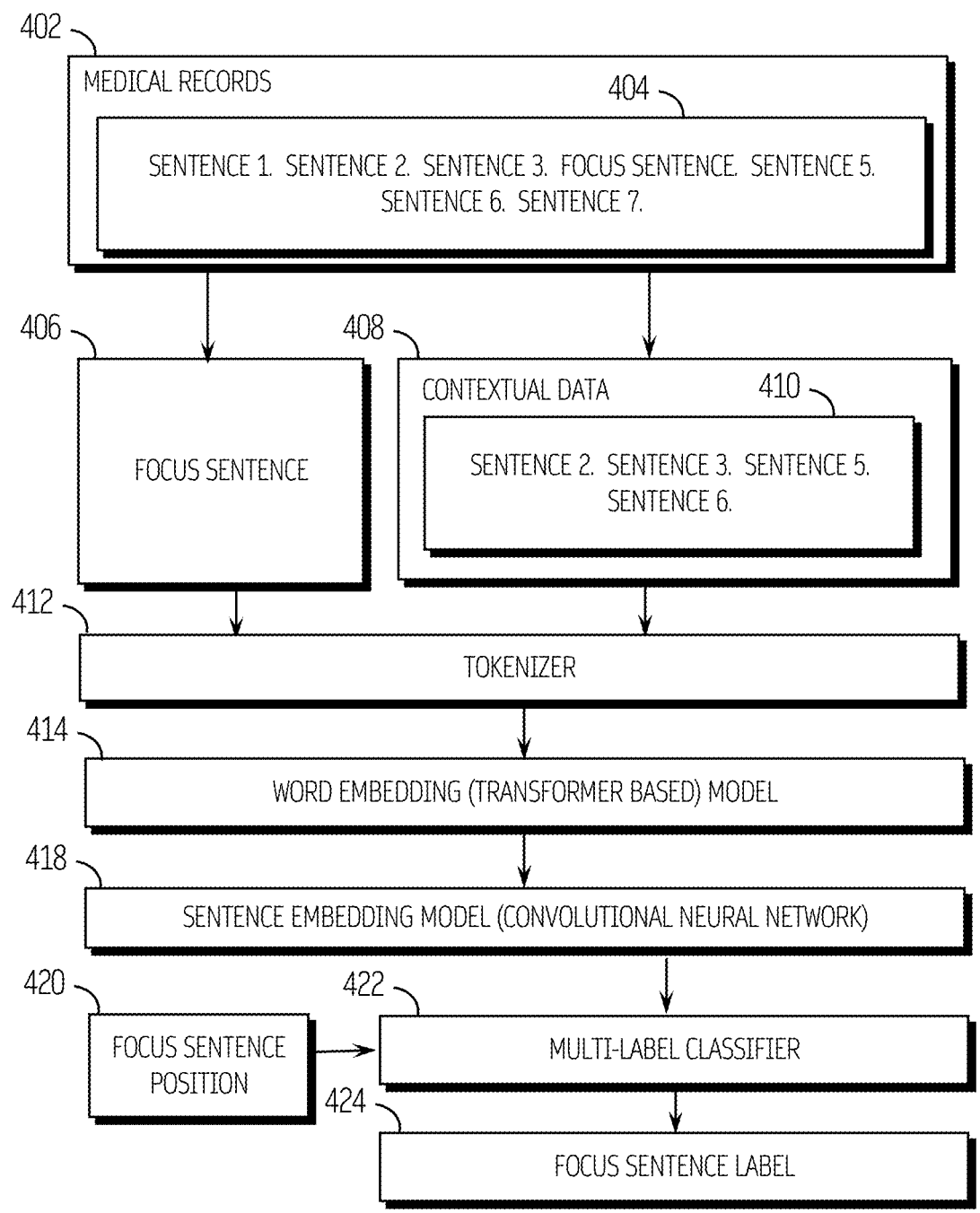
FIG. 4 shows aspects of an apparatus for identifying important items in a medical record.

FIG. 4 shows aspects of an apparatus for identifying important items in a medical record. The apparatus may receive medical records 402. The medical records may include text 404 that may be organized into sentences or groups of words. A focus 406 sentence (a sentence to be evaluated) may be identified in the medical record. Based on the location of the focus sentence 406, contextual data may be identified in the text 404 of the medical record. The contextual data 408 may include sentences 410 from the text 404 of the medical record that are before and/or after the focus sentence. The apparatus may include a tokenizer 412 for parsing the focus sentence 406 and the contextual data 408. The tokenizer 412 may divide the focus and/or contextual data into tokens such as words or phrases. In some cases, the tokenizer 412 may further include tags or special tokens to identify or mark the focus sentence 406 and the contextual data 408. In some cases, the tokenizer 412 may add separators (special tags, reserved words, reserved embedding vectors, and the like) between the focus sentence 406 and the contextual data 408 such that the words/embeddings of the focus sentence may be identifiable from the contextual data 408. In some cases, the tokenizer may further be configured to remove punctuation, remove capitalization, identify headers denoting sections, and the like.

The apparatus may include a word embedding model such as a transformer-based model 414 that processes the output from the tokenizer 412 and determines embeddings related to the focus sentence 406, contextual data 408, and/or special tokens. In embodiments, the embeddings may be contextual. The apparatus may further include a sentence embedding model such as a convolutional neural network 418 for further processing the contextual embeddings 416 to determine sentence embeddings. In embodiments, the sentence embedding model may process words. The apparatus may further include a multi-label classifier such as a linear classifier 422. The multi-label classifier 422 may receive the output of the sentence embedding model 418 and generate a sentence label 424. The label 424 may be a number or a tag that provides an identification of the determined importance of the focus sentence and/or a category of the focus sentence.

In some embodiments, the multi-label classifier 422 may receive additional inputs. In one example, inputs to the multi-label classifier 422 may include a focus sentence position 420. The focus sentence position 420 may identify the position of the focus sentence in the medical record text 404. In one example, the focus sentence position 420 may be the sentence number (such as an indication that the focus sentence is the fourth sentence in the text 404) or a relative position of the focus sentence in the text 404 (such as a normalized number between 0 and 1). The linear classifier 422 may determine the focus sentence label 424.

In embodiments, the systems and apparatus described herein may require training. In embodiments, the components of the system, such as the word embedding model, sentence embedding model, multi-label classifiers, and the like, may require training. Training may be required to improve the accuracy of the focus sentence labels. In some cases, models may be pretrained (such as on generic language data or for generic medical records) but may be further trained on medical records from a specific institution, for a specific medical field, and the like. In some embodiments, all three components may be trained using labeled medical records. In some embodiments, only the multi-label classifier or the sentence embedding model may be trained using labeled medical records, and the word embedding model may be a pre-trained model that was trained on a general language corpus.

Figure 5:
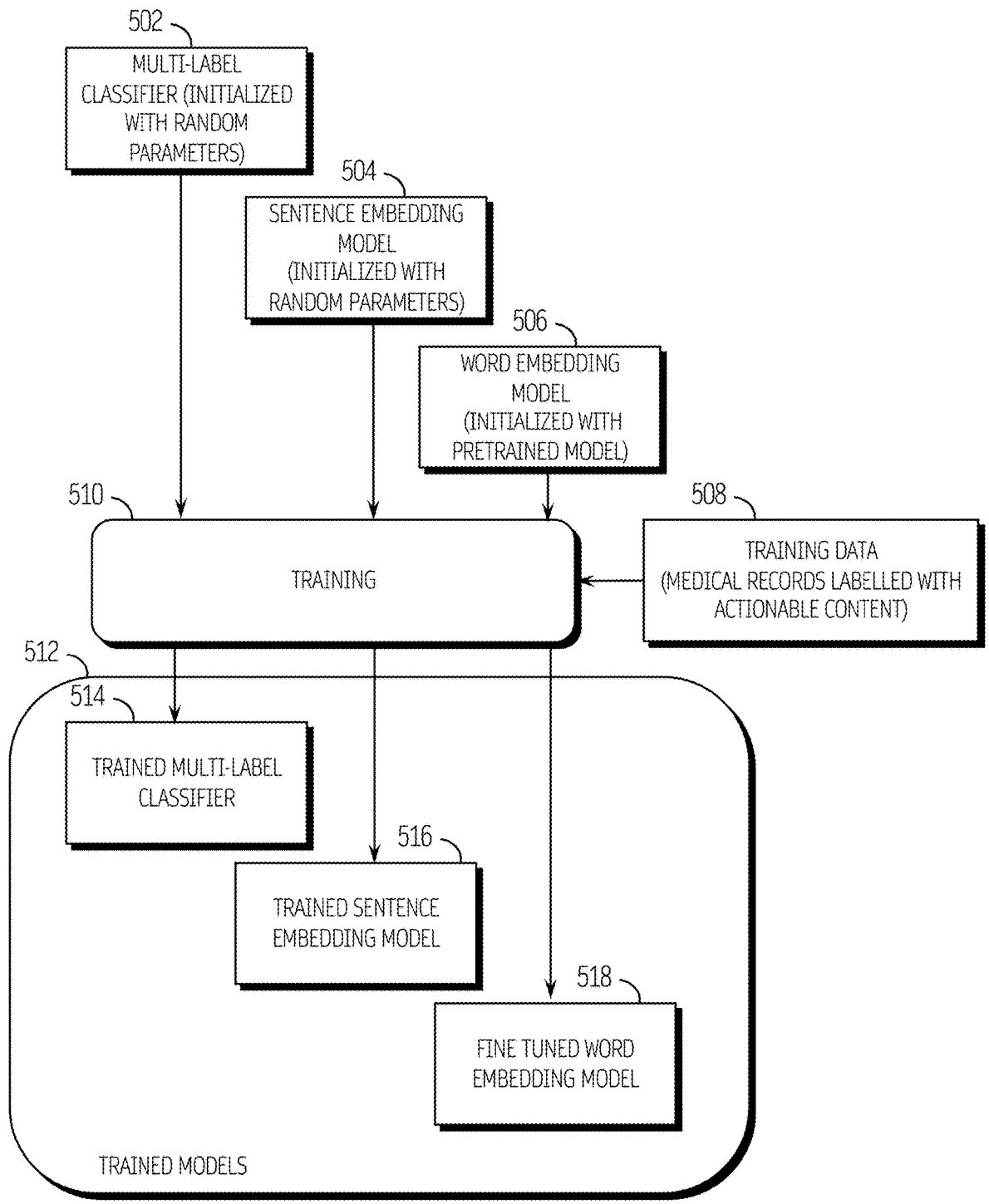
FIG. 5 is a schematic diagram depicting aspects of training the models.

FIG. 5 is a schematic diagram depicting aspects of training. In embodiments, training of models 510 may be based on training data 508 that include medical records labeled with actionable content. Training may include training of one or more of the multi-label classifier 502, sentence embedding model 504, and/or the word embedding model 506. In embodiments, the word embedding model (506 may be initialized with a pretrained model. The model may be pretrained on general language sources such as books, Wikipedia articles, and the like. In some cases, the model may be pretrained on general medical text and/or medical records. In embodiments, the multi-label classifier 502 and the sentence embedding model 504 may be initialized with random parameters. After training 510 using the training data 508, the models may be trained models 512. The training may result in a trained multi-label classifier 514, trained sentence embedding model 516, and a fine-tuned word embedding model 518.

In embodiments, training techniques may include supervised training. The training may comprise multiple rounds where each round updates the parameters of the models by minimizing a loss function. Training may include training using stochastic gradient descent. At each round, a forward pass may be performed using the training data. An error may be computed based on the predicted labels and expected labels. A backward pass may be performed to update the parameters of the models. This training process may proceed until a suitable stopping or convergence criterion is reached.

In embodiments, training may include training the word embedding model, the sentence embedding model, and the multi-label classifier together such that the parameters of the models are updated together. In one example, models may be trained together using stochastic gradient descent.

The training data may be manually labeled by people. In one example, training data may include data from user interactions with highlighted data as described herein. User interactions with medical records that include identified important items may be tracked and used as training data. Interactions such as selection and/or dismissing selections as described herein may be used to update the parameters of the model.

In one example, training data may be manually annotated discharge summaries from the set of patients that were discharged from the ICU (i.e., survived) and thus brought back to the care of their primary care physician or relevant specialists. The training data may be further split by document id into training, validation, and test sets. Training data may be annotated with categories of important items. In one example, categories may include:

- Appointments: Appointments to be either made by the PCP or monitored to ensure the patient attends them after the patient has been discharged from the hospital.
- Lab tests: Laboratory tests that either have results pending at the time of hospital discharge or need to be ordered by the PCP.
- Procedures: Procedures that the PCP needs to either order, ensure another caregiver orders, or ensure the patient undergoes.
- Medications: Medications that the PCP either needs to prescribe or ensure that the patient is taking correctly, e.g., time-limited medications or new medications that may need a dose adjustment.
- Imaging: Imaging studies that either have results pending at the time of hospital discharge or need to be ordered by the PCP.
- Patient Instructions: Follow-up instructions that are directed to the patient, so the PCP can ensure the patient understands and performs them.
- Other: Other follow-up information that is important to relay to the PCP but does not fall under the other categories (e.g., the need to closely observe the patient's diet or fax results to another provider).

Figure 6:
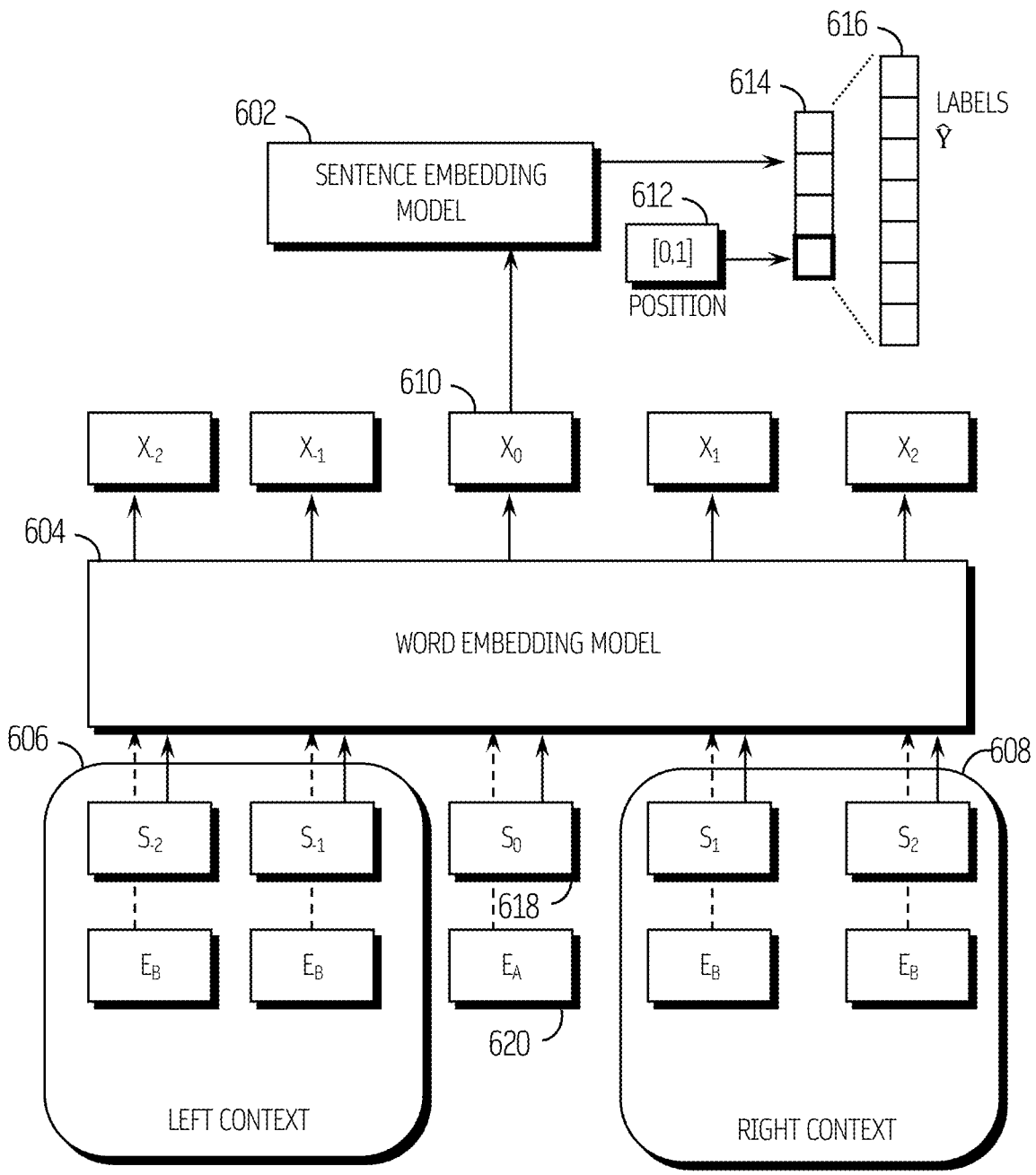
FIG. 6 is a schematic diagram depicting one example embodiment of a trained system for identification of important items.

FIG. 6 is a schematic diagram depicting one example embodiment of a trained system for the identification of important items in a medical record. The system provides for passing a focus sentence and its left and right context through a pre-trained word embedding model, followed by the incorporation of a sentence embedding model 602 and a multi-label classifier 614 to make the final prediction.

The system may receive a focus sentence $S_0$ 618. A tag $E_A$ 620 that identifies the sentence as a focus sentence may be associated with sentence 618. The system may further receive context information which may include left context 606 and right context 608. Each of the left and right contexts may include two sentences that are before ($S_{-2}$ and $S_{-1}$) and two sentences that are after ($S_1$ and $S_2$) the focus sentence 618 in the medical text. The context data 606, 608 may include tags or embeddings ($E_B$) that identify the sentences as relating to context. The input 618, 620, 606, 608 may be processed by a trained word embedding model 604, which may be fine-tuned on clinical data. The word embedding model 604 may output contextual embeddings of the input sentences. The contextual embedding $X_0$ of the focus sentence $S_0$ may be further passed through a sentence embedding model 602 and a multi-label classifier 614 to generate labels 616 that categorize the focus sentence. In some embodiments of the system, the sentence embedding model 602 may also process the contextualized embeddings ($X_{-2}$, $X_{-1}$, $X_1$, $X_2$) of the context sentences ($S_{-2}$, $S_{-1}$, $S_1$, $S_2$). In some cases, position information 612 may be an input to the multi-label classifier 614. The position information may identify the position (absolute or relative) of the focus sentence 618 in the medical text.

Figure 7:
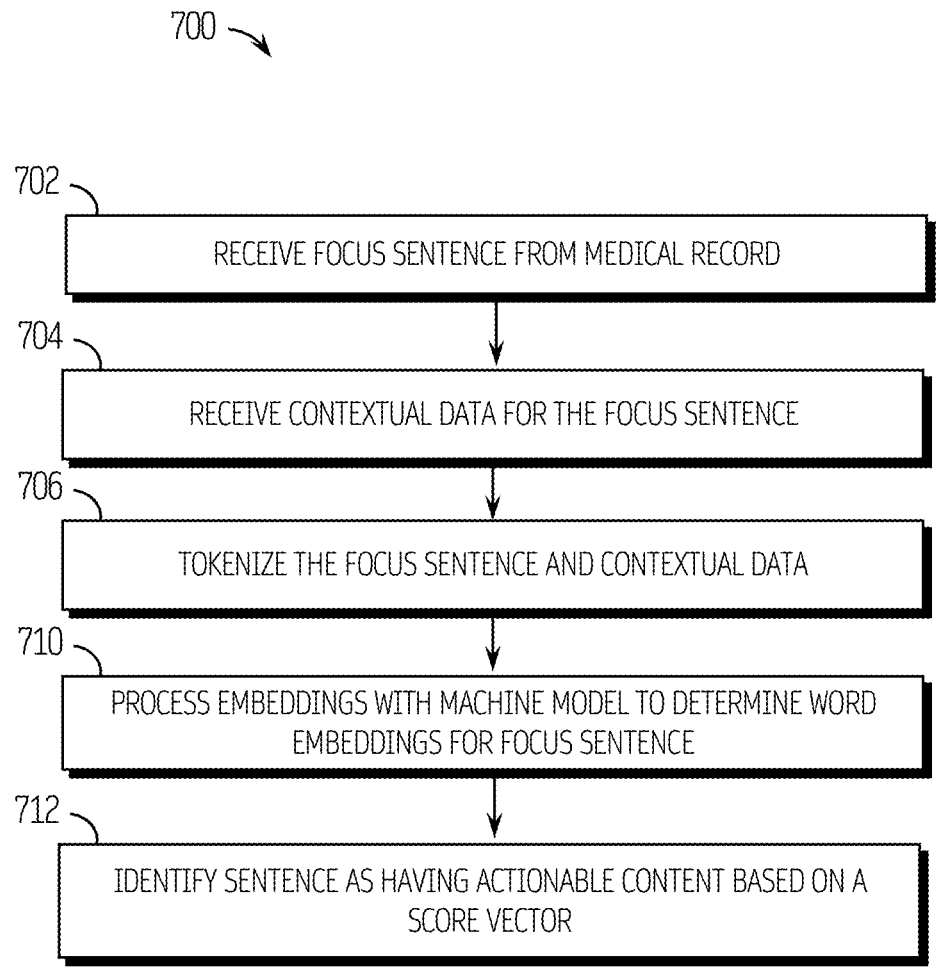
FIG. 7 is a flow diagram of a method for identifying important items from a medical record.

FIG. 7 is a flow diagram showing aspects of a method 700 for identifying important items from a medical record. The method may include receiving focus sentences from a medical record 702. The method may further include receiving contextual data for the focus sentence 704. The focus sentence may be tokenized 706. Tokenization 706 may be into words or phrases and may include additional processing such as filtering, capitalization, and the like. The tokenized data may be processed with a trained machine model to determine word embeddings 710. The word embeddings may be determined for the focus sentence and, in some cases, the contextual data. The word embeddings may be processed to identify if the focus sentence has actionable content based on a score vector 712. The score vector may be determined by a trained model such as a multi-label classifier.

The systems and methods described herein provide for improved identification of important items such as actionable items compared to other methods. Table 1 shows F1 scores on the test set for different categories. The table compares identification of important words using a Bag-of-words model, a CNN, BERT model (pretrained only, without fine-tuning on medical data), a clinical BERT (CBERT, fine-tuned BERT model), CBERT with context, CBERT-Context-CNN, and Full model (CBERT-Context-CNN and sentence position). The table shows that the best model exploits three methods to improve predictions: fine-tuning on unlabeled discharge summaries, incorporating neighboring context from neighboring sentences, and exploiting local textual clues via convolution. Table 1 shows that the CBERT model with the addition of Context, CNN, and position information improves a system's ability to identify actionable content and improves the technology of multi-label item recognition.

TABLE 1

| Model | Imaging | Appt | Medication | Procedure | Lab | Patient | Other |
|---|---|---|---|---|---|---|---|
| Bag-of-words | 0.27 | 0.74 | 0.32 | 0.19 | 0.34 | 0.72 | 0.07 |
| CNN | 0.28 | 0.76 | 0.35 | 0.22 | 0.42 | 0.73 | 0.03 |
| BERT | 0.36 | 0.83 | 0.33 | 0.33 | 0.42 | 0.76 | 0.10 |
| CBERT | 0.46 | 0.81 | 0.42 | 0.54 | 0.54 | 0.76 | 0.24 |
| CBERT-Context | 0.49 | 0.82 | 0.43 | 0.42 | 0.53 | 0.80 | 0.23 |
| CBERT-Context-CNN | 0.44 | 0.84 | 0.41 | 0.44 | 0.52 | 0.79 | 0.15 |
| Full Model | 0.51 | 0.84 | 0.42 | 0.51 | 0.60 | 0.79 | 0.24 |

Figure 8:
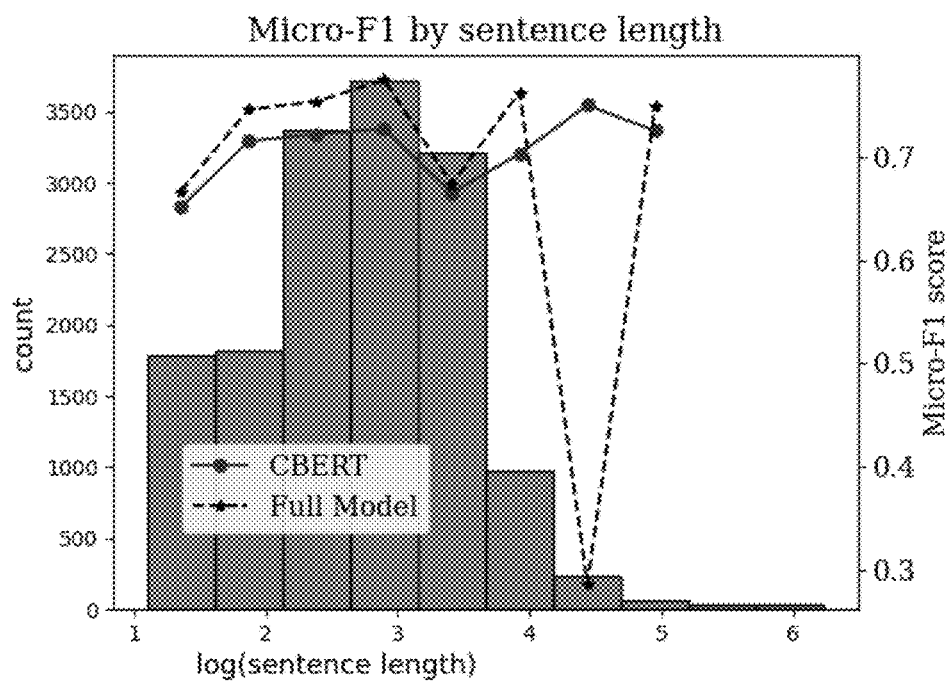
FIG. 8 is a plot showing aspects of performance for two CBERT based models.

FIG. 8 shows a plot of micro-F1 performance for two CBERT based models, superimposed over a histogram of input sentence lengths. To reduce visual noise, the F1 scores for the smallest bin sizes (which correspond to the longest sentences) are suppressed. The graph shows the improved performance of the full model over just a CBERT model over the length of the sentences.

Figure 9:
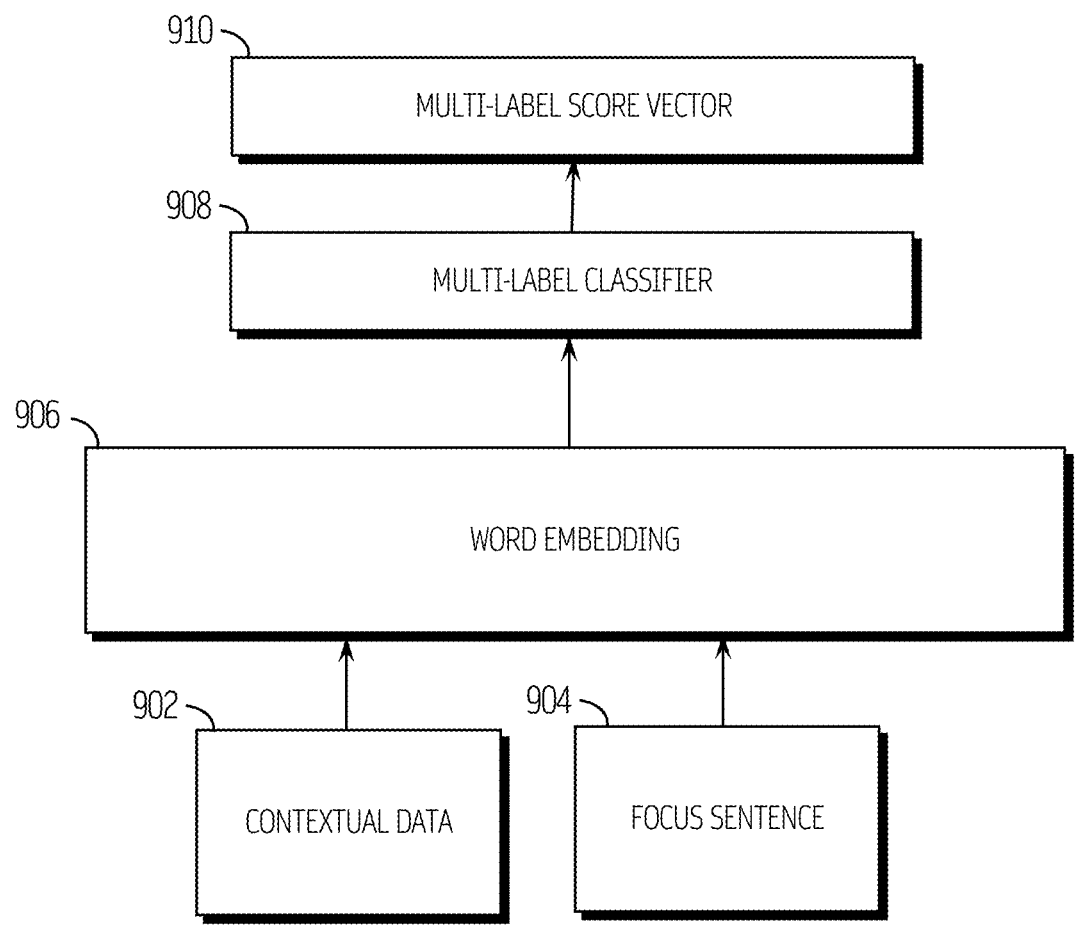
FIG. 9 is a schematic diagram depicting another example embodiment for multi-label sentence classification.

FIG. 9 shows aspects of another example embodiment of a system for multi-label sentence classification. The system may receive words or sentences from the medical record. In one example, the system may receive a focus sentence 904 from the medical record, and the system may output a multi-label score vector 910 that identifies if the focus sentence 904 is related to an important item and may also identify one or more categories of important items. In embodiments, the system may further receive contextual data 902 related to the focus sentence 904. The focus sentence 904 and the contextual data 902 may be separated with special tokens such as separation tokens to distinguish the contextual data from the focus sentence. The system may receive the contextual data 902 and the focus sentence 904 and process the contextual data 902 and the focus sentence 904 using a word embedding model 906 wherein the word embedding model may be any word embedding model described herein. The output of the word embedding model 906 may provide an embedding of the words of the focus and may be contextual. The word embedding model 906 may provide an embedding of the separation tokens.

The system may include a multi-label classifier 908. The multi-label classifier 908 may be a linear classifier that may be configured to determine a multi-label score vector 910 wherein each value of the score vector 910 identifies a score that provides a measure of how close the focus sentence 904 is to a category of important items that should be emphasized or extracted from a medical record. In embodiments, the multi-label classifier may be a logistic regression classifier and may include a linear layer followed by a sigmoid function. The multi-label classifier may receive as input the embedding of the special token that is the output of the word embedding model 906.

Figure 10:
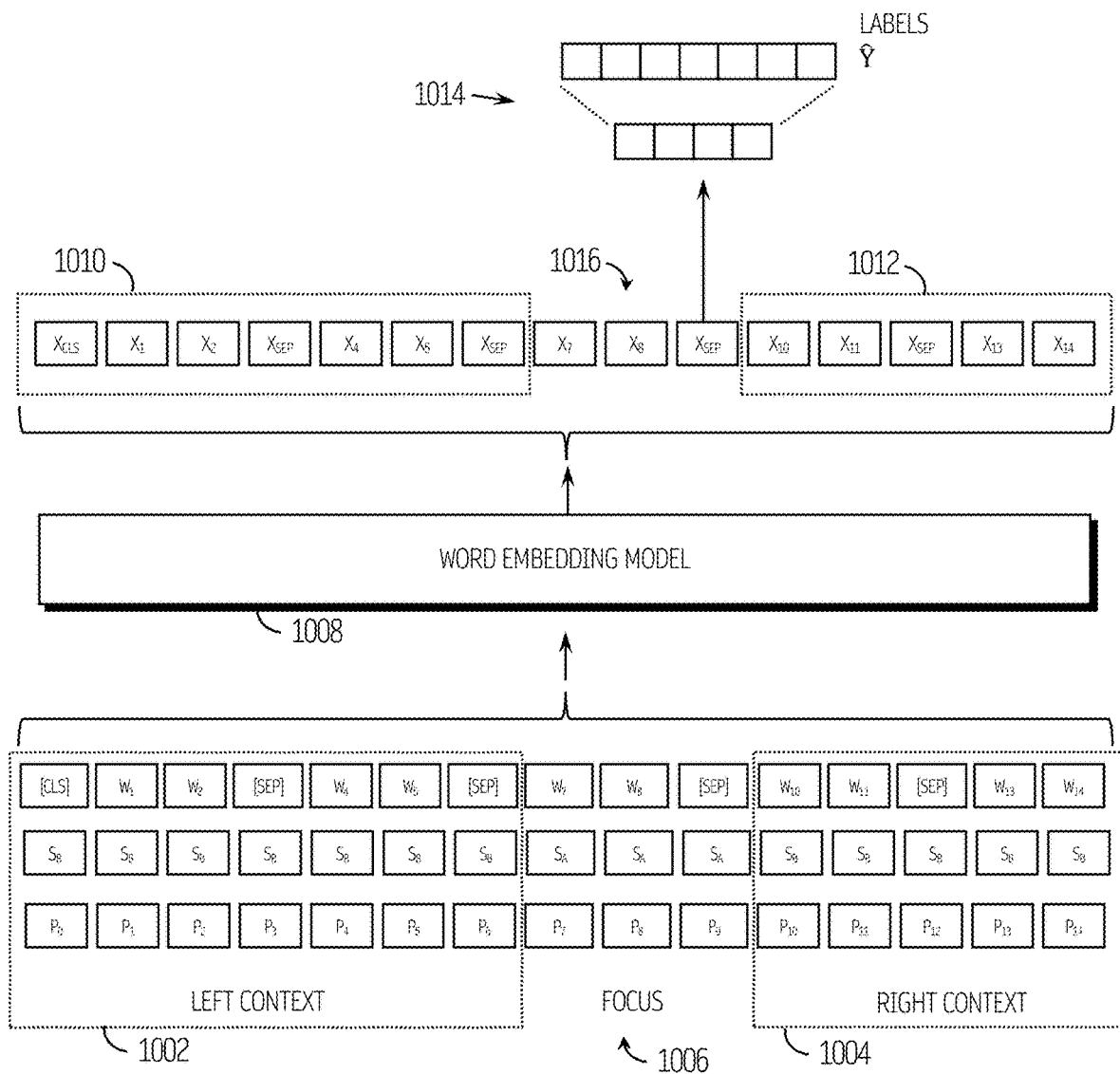
FIG. 10 is a schematic diagram depicting another example embodiment of a system for identification of important items.

FIG. 10 is a schematic diagram depicting another example embodiment of a trained system for the identification of important items in a medical record. The system provides for passing a focus sentence and its left and right context through a pre-trained word embedding model such as a BERT model 1008, followed by a multi-label classifier 1014. The system may receive words for a focus sentence ($W_7$, $W_8$) 1006 and words for a left context ($W_1$, $W_2$, $W_3$, $W_4$) 1002 and right context ($W_{11}$, $W_{18}$, $W_{11}$, $W_{14}$) 1004. The sentences may be separated with separation tokens ([SEP] tokens) that identify where each sentence begins and/or ends. Additional tags may further identify if each word and token is associated with the focus data ($S_A$) or with the context data ($S_B$). In embodiments, the input may further include position data associated with each word and token ($P_0$-$P_{14}$). The input data 1002, 1004, 1006 may be processed by a word embedding model such as BERT 1008, which may be a BERT model fine-tuned on clinical data. The word embedding model 1008 may output contextual embeddings of words ($X_1$-$X_{14}$) and tokens ($X_{CLS}$, $X_{sep}$). The contextual embedding of the separation token $X_{SEP}$ of the focus sentence 1016 may be further passed through a multi-label classifier 1014 to generate labels that categorize the focus sentence. In some embodiments, other tokens such as the embeddings of the [CLS] token ($X_{CLS}$) may be used as the sentence-level representation and used as input to the trained multi-label classifier 1014.

Figure 11:
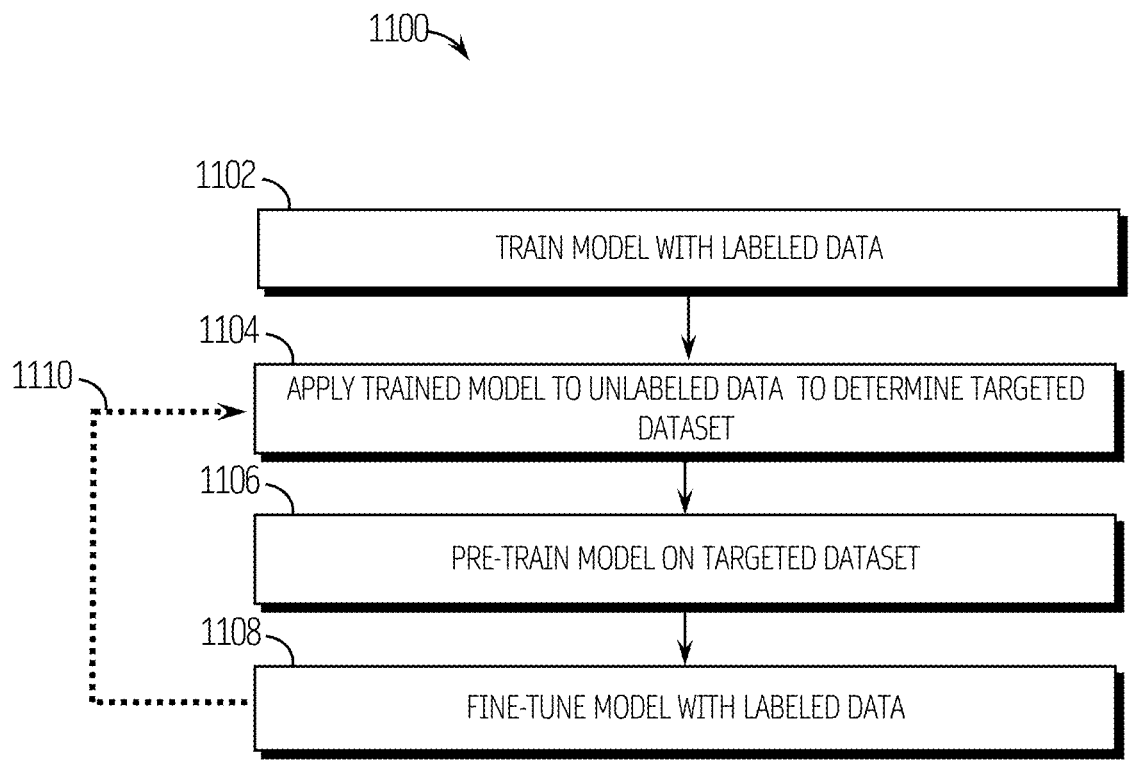
FIG. 11 is a flow diagram of a method for task-targeted pretraining.

FIG. 11 is a flow diagram depicting aspects of training the systems and models from FIGS. 2, 4, 6, and 9-10 using semi-supervised approaches. In embodiments, training may include task-targeted pretraining (TTP). TTP may require fewer data and computation compared to traditional training techniques while attaining comparable performance. TTP surfaces unlabeled sentences that may be positive examples. The positive examples may be used to pre-train the models using auxiliary tasks. In embodiments, method 1100 may include training a word embedding model or systems described with respect to FIGS. 2, 4, 6, and 9-10 with labeled data 1102. The labeled data may be sentences from medical records that are labeled as important and may be associated with categories of important data. The method may further include applying the trained model to unlabeled data 1104 to generate a targeted dataset. The trained model may be applied to unlabeled data, such as medical records, to select sentences that may include important items such as follow-up or action items. The sentences may be selected based using a fixed threshold in the multi-label score vector generated by the model. In one example, if any value of the multi-label score vector is above a threshold value, the sentence may be selected. The threshold value may be selected to generate a dataset of a desired size. Lowering the threshold may increase the dataset size, while increasing the threshold may decrease the dataset size.

Method 1100 may further include pretraining the model (such as the systems and models described with respect to FIGS. 2, 4, 6, and 9-10) on the targeted dataset 1106. The pretraining of the model may include training with an auxiliary task. In one embodiment, the auxiliary task may include masked language modeling and sentence switching task. In embodiments, sentences from the unlabeled data that are in proximity (neighboring or context sentences) to the sentences in the targeted dataset may be extracted from the medical records and used for the pretraining. During pretraining using masked language modeling, sentences from the targeted dataset may be presented to the model with some tokens in the focus sentence masked. The model may be tasked with predicting the masked words. In one example, each token in the focus sentences may be masked with a probability of 0.15. During pretraining using sentence switching tasks, sentences a focus sentence may be swapped with another randomly chosen sentence from the same document, and the model may be tasked with predicting if the presented sentences correspond to sequential sentences. In one example, the focus sentence may be swapped with another random sentence from the medical record with a probability of 0.25. In one embodiment, cross-entropy losses for both tasks may be summed to compute the total loss for an instance, and the total loss may be used to update the weights of the model using backpropagation and gradient updates. In some embodiments, only one auxiliary task may be used for pretraining. After pretraining, the model may be further fine-tuned using labeled data 1108. The labeled data may be the same data used in the initial training 1102. In some embodiments, the fine-tuned model may be used to further select a new set of sentences for pretraining, and the method may be repeated 1110. The fine-tuned model may be used to detect interesting items in a medical record. It should be appreciated that the task-targeted pretraining as described herein improves model training by reducing the required computational resources, data storage resources, and time required for pretraining. As described herein, task-targeted pretraining involves only a small subset of available data, while traditional methods may require the use of all the available data and may not be feasible in many applications due to computational, storage, and time constraints.

Figure 12:
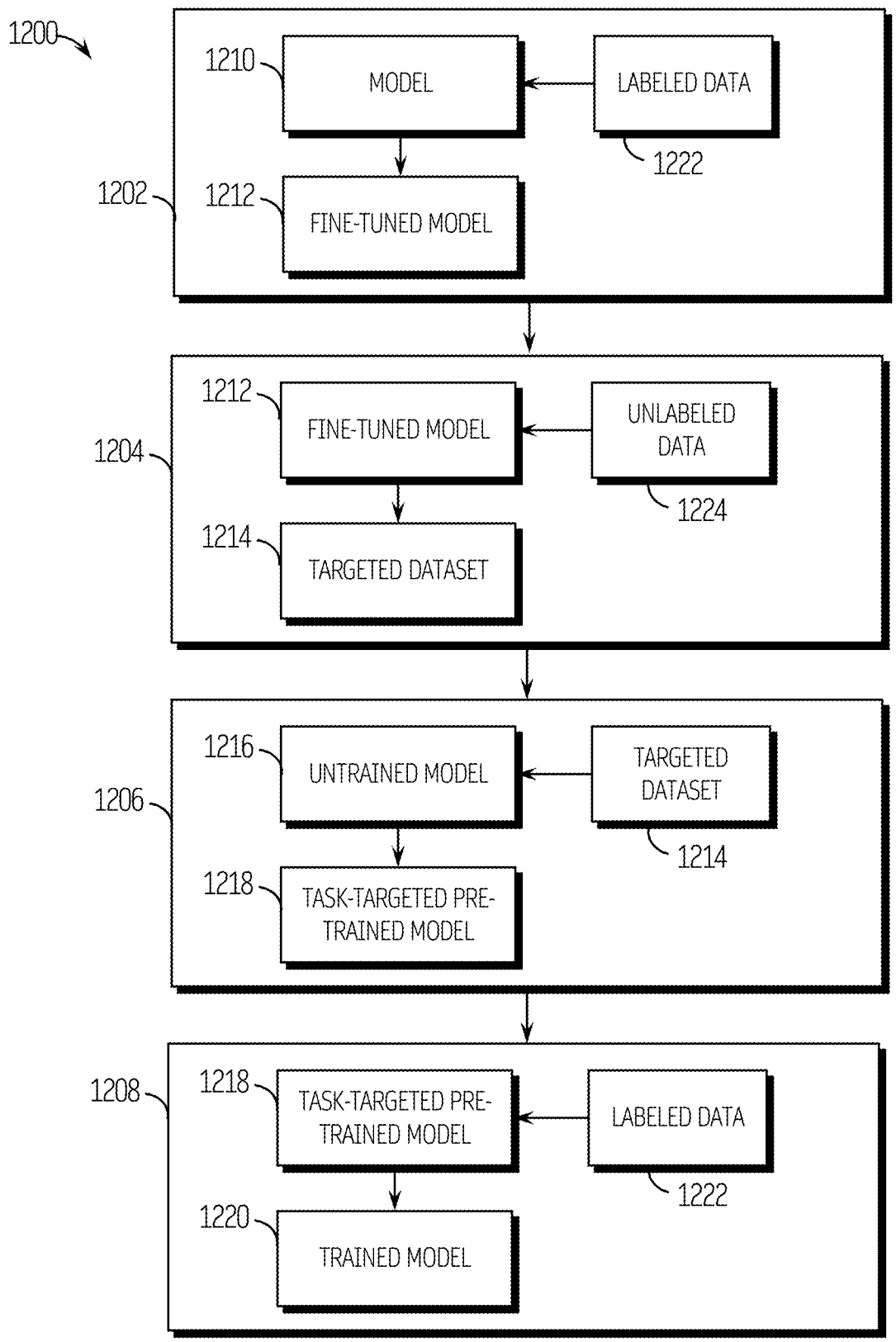
FIG. 12 is a flow diagram of a method for task-targeted pretraining.

FIG. 12 is another flow diagram of a method 1200 for task-targeted pretraining. The method may begin with a step of fine-tuning a general model 1202. A general model 1210 that may have been pre-trained on general or non-field-specific data may be fine-tuned on labeled data 1222. The labeled data 1222 may indicate important items in medical records. The model 1210 may be fine-tuned on the labeled data 1222 to generate a fine-tuned model 1212. In the next step 1204, the fine-tuned model 1212 may be used to generate a targeted dataset 1214. The fine-tuned model 1212 may be used to process unlabeled data 1224 to identify important items and optionally categories of important items from the unlabeled data 1224 to generate a targeted dataset 1214. The targeted dataset may be a subset of sentences of the unlabeled data 1224. The targeted dataset may further include information about context data from the unlabeled data 1224 that may include sentences around important items. In the next step 1206, the targeted dataset 1214 may be used to pre-train an untrained model 1216 to generate a task-targeted pre-trained model 1218. The untrained model 1216 may be pre-trained using auxiliary tasks such as masked language modeling and sentence switching tasks. In step 1208, the task-targeted pre-trained model 1218 may be further fine-tuned using labeled data 1222 to generate a trained model 1220 that may be used to process medical records and identify important items in the records.

In embodiments, various training configurations as described herein may be used to train components of the system. In one embodiment, training may include supervised training only on the multi-label classifier and optionally (if part of the system) on the sentence embedding model. In another embodiment, training may include supervised training of the multi-label classifier and optionally (if part of the system) the sentence embedding model and supervised fine-tuning of the pre-trained word embedding model. In another embodiment, training may include semi-supervised task targeted pretraining on the word embedding model followed by supervised training of the multi-label classifier and optionally (if part of the system) the sentence embedding model followed by supervised fine-tuning of the pre-trained word embedding model.

The methods and systems described herein may be deployed in part or in whole through a machine that executes computer software, program codes, and/or instructions on a processor. "Processor" as used herein is meant to include at least one processor, and unless context clearly indicates otherwise, the plural and the singular should be understood to be interchangeable. Any aspects of the present disclosure may be implemented as a computer-implemented method on the machine, as a system or apparatus as part of or in relation to the machine, or as a computer program product embodied in a computer-readable medium executing on one or more of the machines. The processor may be part of a server, client, network infrastructure, mobile computing platform, stationary computing platform, or other computing platform. A processor may be any kind of computational or processing device capable of executing program instructions, codes, binary instructions and the like. The processor may be or include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more thread. The thread may spawn other threads that may have assigned priorities associated with them; the processor may execute these threads based on priority or any other order based on instructions provided in the program code. The processor may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like.

A processor may include one or more cores that may enhance speed and performance of a multiprocessor. In embodiments, the process may be a dual core processor, quad core processors, other chip-level multiprocessor and the like that combine two or more independent cores (called a die).

The methods and systems described herein may be deployed in part or in whole through a machine that executes computer software on a server, client, firewall, gateway, hub, router, or other such computer and/or networking hardware. The software program may be associated with a server that may include a file server, print server, domain server, internet server, intranet server and other variants such as secondary server, host server, distributed server and the like. The server may include one or more of memories, processors, computer readable media, storage media, ports (physical and virtual), communication devices, and interfaces capable of accessing other servers, clients, machines, and devices through a wired or a wireless medium, and the like. The methods, programs, or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers and the like. Additionally, this coupling and/or connection may facilitate remote execution of program across the network. The networking of some or all of these devices may facilitate parallel processing of a program or method at one or more locations without deviating from the scope of the disclosure. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client and other variants such as secondary client, host client, distributed client and the like. The client may include one or more of memories, processors, computer readable media, storage media, ports (physical and virtual), communication devices, and interfaces capable of accessing other clients, servers, machines, and devices through a wired or a wireless medium, and the like. The methods, programs, or codes as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of program across the network. The networking of some or all of these devices may facilitate parallel processing of a program or method at one or more locations without deviating from the scope of the disclosure. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements.

The methods, program codes, and instructions described herein and elsewhere may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, EVDO, mesh, or other networks types.

The methods, programs codes, and instructions described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer-to-peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The methods and systems described herein may transform physical and/or or intangible items from one state to another. The methods and systems described herein may also transform data representing physical and/or intangible items from one state to another.

The elements described and depicted herein, including in flow charts and block diagrams throughout the figures, imply logical boundaries between the elements. However, according to software or hardware engineering practices, the depicted elements and the functions thereof may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipment, servers, routers and the like. Furthermore, the elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps thereof, may be realized in hardware, software or any combination of hardware and software suitable for a particular application. The hardware may include a general-purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine-readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

All documents referenced herein are hereby incorporated by reference in the entirety.

What is claimed is:

1. A method for identifying actionable content from a medical record, the method comprising:
    retrieving a focus sentence from the medical record;
    retrieving contextual data for the focus sentence from the medical record, wherein the contextual data includes words before and after the focus sentence in the medical record;
    tokenizing the focus sentence and the contextual data;
    determining embeddings for the words of the tokenized focus sentence and the contextual data;
    processing the embeddings with a word embedding model to determined contextualized embeddings of the words in the focus sentence;
    processing the contextualized embeddings with a sentence embedding model to determine a sentence embedding vector for the focus sentence;
    determining a position of the focus sentence in the medical record;
    processing the sentence embedding vector and the position with a multi-label classifier to determine a multi-label score vector, wherein each element of the multi-label score vector is associated with a different type of actionable content;
    assigning at least one type of actionable content to the focus sentence based on values of the elements of the score vector, and
    emphasizing the focus sentence in the medical record according to the assigned type of actionable content.

2. The method of claim 1, wherein processing with the sentence embedding model includes processing with a convolutional neural network (CNN).

3. The method of claim 1, wherein processing with the word embedding model includes processing with a transformer-based model.

4. The method of claim 1, wherein assigning at least one type of actionable content to the focus sentence includes assigning at least one type selected from the group consisting of: appointment, laboratory test, procedure, medication, imaging, patient instruction, and other.

5. The method of claim 1, wherein retrieving contextual data includes retrieving, from the medical record, one or more sentences before the focus sentence and one or more sentences after the focus sentence.

6. The method of claim 1, further comprising:
initializing the sentence embedding model with random parameters; and
initializing the word embedding model with a pretrained masked language model.

7. The method of claim 6, further comprising:
training the initialized sentence embedding model and the initialized word embedding model using medical records labelled with types of actionable content.

8. The method of claim 1, wherein determining embeddings includes appending segment labels to the embedding of each word, wherein the segment labels identify if each word belongs to the focus sentence or the contextual data.

9. The method of claim 1, wherein determining the position includes determining a relative position of the focus sentence in the medical record.

10. The method of claim 1, wherein emphasizing comprises highlighting the focus sentence according to the assigned type of actionable content.

11. The method of claim 1, further comprising extracting and categorizing the focus sentence according to the assigned type of actionable content.

12. The method of claim 1, assigning at least one type of actionable content to the focus sentence includes assigning a confidence score that the focus sentence includes actionable content.

13. The method of claim 12, wherein emphasizing the focus sentence in the medical record includes emphasizing the focus sentence according to the confidence score.

14. A system, comprising:
at least one server computer comprising at least one processor and at least one memory, the at least one server computer configured to:
retrieve a focus sentence from a medical record;
retrieve contextual data for the focus sentence from the medical record, wherein the contextual data includes words before and after the focus sentence in the medical record;
tokenize the focus sentence and the contextual data;
determine embeddings for the words of the tokenized focus sentence and the contextual data;
process the embeddings with a word embedding model to determined contextualized embeddings of the words in the focus sentence;
determine a position of the focus sentence in the medical record;
process the contextualized embeddings and the position with a sentence embedding model to determine a sentence embedding vector for the focus sentence;
process the sentence embedding vector with a multi-label classifier to determine a multi-label score vector, wherein each element of the multi-label score vector is associated with a different type of actionable content;
assign at least one type of actionable content to the focus sentence based on values of the elements of the score vector; and
emphasize the focus sentence in the medical record according to the assigned type of actionable content.

15. The system of claim 14, wherein processing with the sentence embedding model includes processing with a convolutional neural network (CNN).

16. The system of claim 14, wherein processing with the word embedding model includes processing with a transformer based model.

17. The system of claim 14, wherein assigning at least one type of actionable content to the focus sentence includes assigning at least one type selected from the group consisting of: appointment, laboratory test, procedure, medication, imaging, patient instruction, and other.

18. One or more non-transitory, computer-readable media comprising computer-executable instructions that, when executed, cause at least one processor to perform actions comprising:
retrieving a focus sentence from a medical record;
retrieving contextual data for the focus sentence from the medical record, wherein the contextual data includes words before and after the focus sentence in the medical record;
tokenizing the focus sentence and the contextual data;
determining embeddings for the words of the tokenized focus sentence and the contextual data;
processing the embeddings with a word embedding model to determined contextualized embeddings of the words in the focus sentence;
determining a position of the focus sentence in the medical record;
processing the contextualized embeddings and the position with a sentence embedding model to determine a sentence embedding vector for the focus sentence;
processing the sentence embedding vector with a multi-label classifier to determine a multi-label score vector, wherein each element of the multi-label score vector is associated with a different type of actionable content;
assigning at least one type of actionable content to the focus sentence based on values of the elements of the score vector, and
emphasizing the focus sentence in the medical record according to the assigned type of actionable content.

* * * * *